United States Patent
Harmer et al.

(10) Patent No.: US 9,125,998 B2
(45) Date of Patent: Sep. 8, 2015

(54) INHALER

(75) Inventors: Quentin John Harmer, Cambridge (GB); Ivan Milivojevic, Cambridge (GB); Matthew Neil Sarkar, Cambridge (GB)

(73) Assignee: Vectura Delivery Devices Limited, Chippenham (GB)

( * ) Notice: Subject to any disclaimer, the term of this patent is extended or adjusted under 35 U.S.C. 154(b) by 496 days.

(21) Appl. No.: 12/864,561

(22) PCT Filed: Jan. 14, 2009

(86) PCT No.: PCT/EP2009/050340
§ 371 (c)(1),
(2), (4) Date: Nov. 24, 2010

(87) PCT Pub. No.: WO2009/092650
PCT Pub. Date: Jul. 30, 2009

(65) Prior Publication Data
US 2011/0056488 A1    Mar. 10, 2011

(30) Foreign Application Priority Data
Jan. 24, 2008    (EP) .................................... 08100886

(51) Int. Cl.
*A61M 16/00* (2006.01)
*A61M 15/00* (2006.01)

(52) U.S. Cl.
CPC ......... *A61M 15/0045* (2013.01); *A61M 15/004* (2014.02); *A61M 15/0021* (2014.02); *A61M 15/0028* (2013.01); *A61M 15/0036* (2014.02);
(Continued)

(58) Field of Classification Search
CPC .......... A61M 2206/16; A61M 15/021; A61M 15/0028; A61M 15/0036; A61M 15/004; A61M 15/0045; A61M 15/0051; A61M 2202/064

USPC ........................... 128/203.19, 203.21, 203.15
See application file for complete search history.

(56) References Cited

U.S. PATENT DOCUMENTS

| 3,807,400 A | 4/1974 | Cocozza |
| 3,906,950 A | 9/1975 | Cocozza |

(Continued)

FOREIGN PATENT DOCUMENTS

| CA | 2497059 A1 | 3/2004 |
| CN | 1437551 A | 8/2003 |

(Continued)

OTHER PUBLICATIONS

International Search Report issued in connection with international Patent Application No. PCT/EP2009/050340.
(Continued)

*Primary Examiner* — Melanie Hand
*Assistant Examiner* — Aundria Hairell
(74) *Attorney, Agent, or Firm* — Davidson, Davidson & Kappel

(57) ABSTRACT

An inhaler for producing an inhalable aerosol of powdered medicament is disclosed. The inhaler includes an aerosolizing device having a chamber of substantially circular cross-section, inlet and outlet ports at opposite ends of the chamber for the flow of drug laden air through the chamber between said ports and, a bypass air inlet for the flow of clean air into the chamber. The bypass air inlet is configured so that air entering the chamber through said inlet forms a cyclone in the chamber that interacts with the drug laden air flowing between the inlet and outlet ports.

27 Claims, 4 Drawing Sheets

(52) U.S. Cl.
CPC ..... *A61M 15/0051* (2014.02); *A61M 2202/064* (2013.01)

(56) References Cited

U.S. PATENT DOCUMENTS

| | | | |
|---|---|---|---|
| 4,210,140 A | 7/1980 | James et al. | |
| 4,338,931 A | 7/1982 | Cavazza | |
| 4,423,724 A | 1/1984 | Young | |
| 5,070,870 A * | 12/1991 | Pearce | 128/203.15 |
| 5,301,666 A | 4/1994 | Lerk et al. | |
| 5,476,093 A * | 12/1995 | Lankinen | 128/203.15 |
| 5,533,505 A | 7/1996 | Kallstrand et al. | |
| 5,676,130 A | 10/1997 | Gupte et al. | |
| 5,881,719 A | 3/1999 | Gottenauer et al. | |
| 5,947,118 A | 9/1999 | Hochrainer et al. | |
| 6,138,668 A | 10/2000 | Patton et al. | |
| 6,230,707 B1 | 5/2001 | Hoerlin | |
| 6,347,629 B1 * | 2/2002 | Braithwaite | 128/203.15 |
| 6,367,471 B1 * | 4/2002 | Genosar et al. | 128/200.23 |
| 6,367,473 B1 | 4/2002 | Kafer | |
| 7,225,808 B2 | 6/2007 | Davies et al. | |
| 7,258,119 B2 | 8/2007 | Mazzoni | |
| 7,344,734 B2 | 3/2008 | Heijerman et al. | |
| 7,814,905 B2 | 10/2010 | Schuler et al. | |
| 7,832,399 B2 | 11/2010 | Ganem et al. | |
| 8,181,647 B2 | 5/2012 | Ishizeki et al. | |
| 2002/0088463 A1 | 7/2002 | Keane et al. | |
| 2003/0053960 A1 * | 3/2003 | Heijerman et al. | 424/46 |
| 2003/0140923 A1 | 7/2003 | Taylor et al. | |
| 2003/0188747 A1 | 10/2003 | Ohki et al. | |
| 2004/0107963 A1 | 6/2004 | Finlay et al. | |
| 2004/0149283 A1 | 8/2004 | Hochrainer | |
| 2004/0153033 A1 | 8/2004 | Mazzoni | |
| 2005/0161041 A1 | 7/2005 | Schuler et al. | |
| 2005/0183723 A1 | 8/2005 | Pinon et al. | |
| 2006/0147389 A1 * | 7/2006 | Staniforth et al. | 424/46 |
| 2006/0185672 A1 | 8/2006 | Pinon et al. | |
| 2006/0254583 A1 * | 11/2006 | Deboeck et al. | 128/203.15 |
| 2007/0107722 A1 | 5/2007 | Hoelz et al. | |
| 2007/0125375 A1 * | 6/2007 | Finlay et al. | 128/203.15 |
| 2007/0137645 A1 * | 6/2007 | Eason et al. | 128/203.15 |
| 2007/0295332 A1 | 12/2007 | Ziegler et al. | |
| 2008/0314384 A1 * | 12/2008 | Harris et al. | 128/203.15 |
| 2010/0000529 A1 * | 1/2010 | Prime et al. | 128/203.15 |
| 2011/0120463 A1 | 5/2011 | Esteve et al. | |

FOREIGN PATENT DOCUMENTS

| | | |
|---|---|---|
| CN | 1671436 | 9/2005 |
| CN | 1678406 A | 10/2005 |
| CN | 1867369 A | 11/2006 |
| DE | 69319100 T2 | 1/1999 |
| DE | 10239443 A1 | 3/2004 |
| DE | 102005054383 A1 | 5/2007 |
| EP | 0041783 B1 | 12/1981 |
| EP | 0041783 B1 | 12/1984 |
| EP | 0547429 A1 | 6/1993 |
| EP | 0911047 A1 | 5/1994 |
| EP | 0835148 A1 | 4/1998 |
| EP | 1129705 A1 | 9/2001 |
| EP | 1 649 886 | 4/2006 |
| EP | 176008 A1 | 3/2007 |
| FR | 2224175 | 10/1974 |
| GB | 2407042 | 4/2005 |
| JP | S5048782 | 5/1975 |
| JP | 53100695 | 9/1978 |
| JP | H0223192 B2 | 5/1990 |
| JP | H07-501231 A | 2/1995 |
| JP | 2000-504248 A | 4/2000 |
| JP | 2001-70403 A | 3/2001 |
| JP | 3223300 B2 | 10/2001 |
| JP | 2003535656 | 12/2003 |
| JP | 2004-529664 A | 9/2004 |
| JP | 2004530498 | 10/2004 |
| JP | 2005-506855 A | 3/2005 |
| JP | 2006-502759 | 1/2006 |
| JP | 2006-507876 A | 3/2006 |
| JP | 2007-014744 A | 1/2007 |
| JP | 2007-533363 A | 11/2007 |
| TW | 200613021 | 5/1994 |
| WO | 89/07464 | 8/1989 |
| WO | WO93/18811 A1 | 9/1993 |
| WO | WO 97/27892 A1 | 8/1997 |
| WO | 01/07107 | 2/2001 |
| WO | WO01/98174 A1 | 12/2001 |
| WO | WO02/00280 A2 | 1/2002 |
| WO | WO02/089880 A2 | 11/2002 |
| WO | WO 03000325 | 1/2003 |
| WO | WO2004/050152 A1 | 6/2004 |
| WO | WO2005/025656 A1 | 3/2005 |
| WO | WO2005/037353 A1 | 4/2005 |
| WO | WO2006/026237 A1 | 3/2006 |
| WO | WO2006/108877 A2 | 10/2006 |
| WO | WO 2008/051621 A2 | 5/2008 |

OTHER PUBLICATIONS

Written Opinion of the international Searching Authority issued in connection with International Patent Application No. PCT/EP2009/050340.

Office Action, dated Oct. 29, 2013, issued by the Japanese Patent Office in connection with Japanese Application No. 2011-546807, and English translation thereof.

* cited by examiner

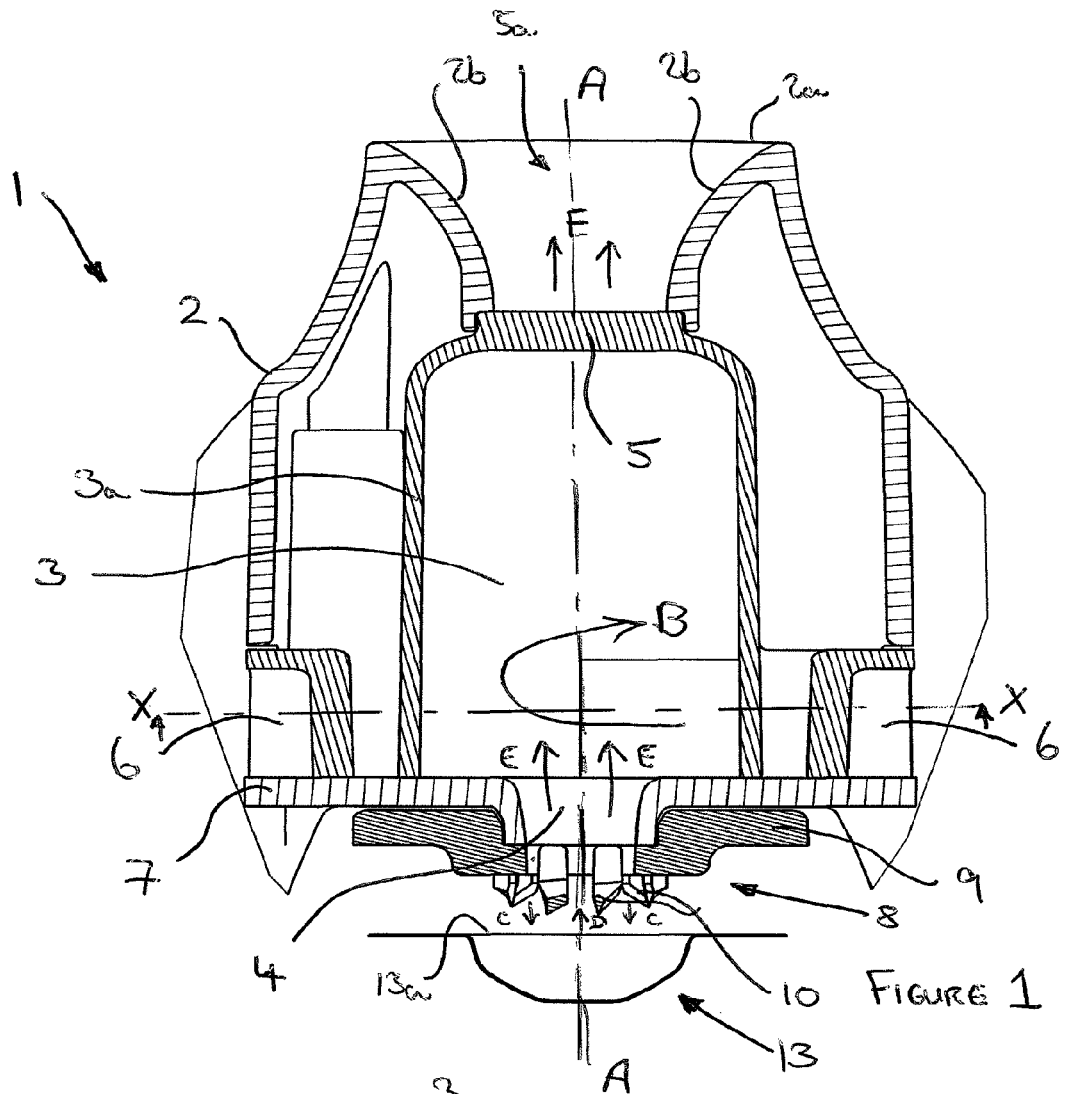
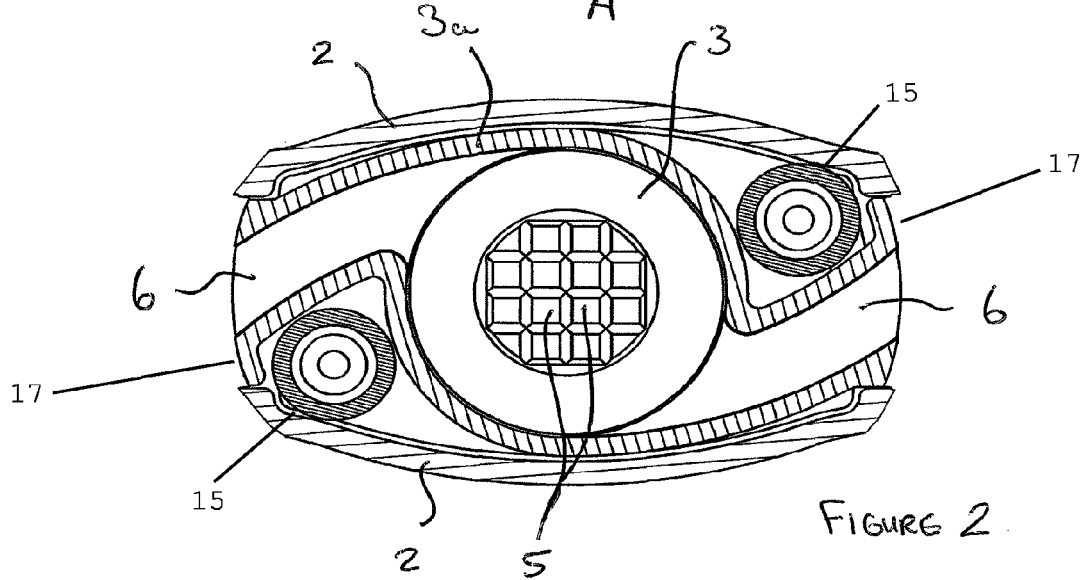

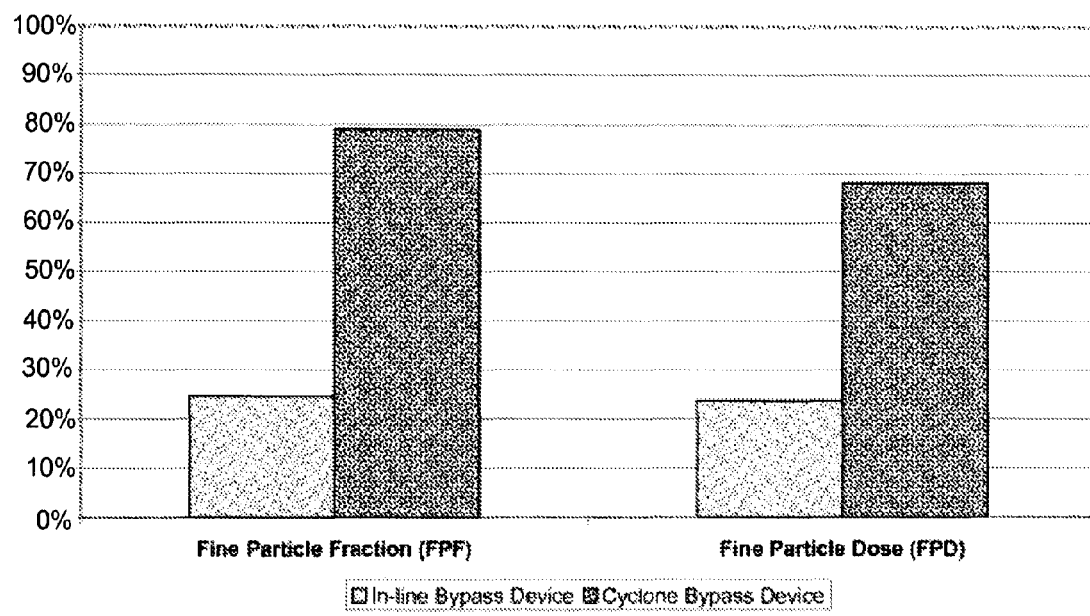

INHALER

This application is a national phase application under 35 U.S.C. §371 of International Application No. PCT/2009/050340, filed Jan. 14, 2009, which claims priority to European Patent Application No. 08100886.4, filed Jan. 24, 2008, the disclosures of which are all hereby incorporated by reference herein.

The present invention relates to inhalers and, in particular, to inhalers for the delivery of dry powder medicament to the lung.

Oral or nasal delivery of a medicament using an inhalation device is a particularly attractive method of drug administration as these devices are relatively easy for patients to use discreetly and in public. As well as delivering medicament to treat local diseases of the airway and other respiratory problems, they have more recently been used to deliver drugs to the bloodstream via the lungs, thereby avoiding the need for hyodermic injections.

For a medicament in particulate form, the provision of an inhalable aerosol requires an inhaler that can produce a repeatable dose of fine particles. In order for the particles of medicament to reach the deep lung area (alveoli) and thus be absorbed into the bloodstream, the particles must have an effective diameter in the range of approximately 1 to 3 microns. The portion of the emitted aerosol which includes this range of particle size is known as the "fine particle fraction" (FPF). If the particles are larger than 5 microns, they may not be transported by the inhaled airflow deep into the lung, because they are likely to be trapped in the respiratory passages before reaching the deep lung. For example, particles of the order of 10 microns are unlikely to progress further than the trachea and particles of the order of 50 microns tend to deposit on the back of the throat when inhaled. Furthermore, if the particles are less than 1 micron in effective diameter, the particles may not be absorbed into the lung, because they are small enough to be expelled from the lung with the exhaled airflow.

The efficiency of a dry powder inhaler may be measured in terms of the fine particle dose (FPD) or the FPF. The FPD is the total mass of active agent which is emitted from the device following actuation which is present in an aerodynamic particle size smaller than a defined limit. This limit is generally taken to be 5 microns although particles having a diameter less than 3 microns are preferred, for the reasons stated above. The FPD is measured using an impactor or impinger, such as a twin stage impinger (TSI), multi-stage impinger (MSI), Andersen Cascade Impactor (ACI) or a Next Generation Impactor (NGI). Each impactor or impinger has a pre-determined aerodynamic particle size collection cut points for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

The FPF is normally defined as the FPD divided by the emitted or delivered dose which is the total mass of active agent that is emitted from the device following actuation and does not include powder deposited inside or on the surfaces of the device. The FPF may also, however, be defined as the FPD divided by the metered dose which is the total mass of active agent present in the metered form presented by the inhaler device in question. For example, the metered dose could be the mass of active agent present in a foil blister.

In conventional inhalers, the emitted dose (the amount of medicament that enters the patient's airway) is around 80% to 90% of the dose ejected from the inhaler. However, the FPF may only be around 50% of the emitted dose but the variation in the respirable dose of known inhalers can be +/−20 to 30%. Such variation is generally acceptable in the case of asthma drugs and the like. However, it will be appreciated that for the pulmonary delivery of systemic small molecule and protein and peptide drugs or for the administration of drugs such as insulin, growth hormone or morphine, this amount of variation in respirable dose is unacceptable. This is not only because it is considerably more important to ensure that the patient receives the same intended dose of these types of drugs each time the inhaler is used, so that a predictable and consistent therapeutic effect is achieved, but a relatively low respirable dose represents a significant wastage of what may be an expensive drug.

It will therefore be appreciated that for systemic pulmonary delivery, the provision of an inhalable aerosol requires an inhaler that can deliver the drug in a highly efficient, accurate and repeatable manner leading to a more predictable and consistent therapeutic effect which minimises any potentially harmful side effects for the patient as well as reducing the amount of costly drug required to deliver a therapeutic dose.

To ensure that a powdered medicament is delivered with an accurately controlled range of particle sizes in order that they are absorbed effectively in the lung, it is necessary to deagglomerate the particles as they flow through the device prior to entry into the patient's airway.

It is known to separate particles of medicament by generating shear forces between the particles, for example by providing a substantial velocity gradient across the particles. One way to achieve this is to provide the inhaler with a cyclone chamber having an axial outlet and a tangential inlet. The drug is entrained in an airflow and allowed to enter the cyclone chamber through the tangential inlet. The high shear forces generated between the particles as they spin around the chamber in the airflow are sufficient to break-up agglomerates of particles before they pass out of the chamber through the outlet. An inhaler having a cyclone chamber is known from the Applicant's own earlier patent EP1191966 B1. A device for the pulverisation of particles or agglomerates of a powdered inhalation medicament is also known from EP0477222 A1. The device disclosed in this document comprises a rotationally symmetrical vortex chamber with spaced inlet and outlet ports. The inlet ports direct drug laden air into the vortex chamber in a direction at a tangent or close to a tangent of the chamber.

The present invention seeks to provide an inhaler which is capable of reliably generating an inhalable aerosol of a powdered medicament with an effective particle size that is sufficiently small for the medicament to be delivered to and absorbed into the lungs of a patient.

According to the invention, there is provided an inhaler for producing an inhalable aerosol of powdered medicament including an aerosolising device having a chamber of substantially circular cross-section, inlet and outlet ports at opposite ends of the chamber for the flow of drug laden air through the chamber between said ports and, a bypass air inlet for the flow of clean air into the chamber, said bypass air inlet being configured so that air entering the chamber through said inlet forms a cyclone in the chamber that interacts with the drug laden air flowing between the inlet and outlet ports.

Preferably, the bypass air inlet is arranged so that air enters the chamber through said inlet substantially tangential to the wall of the chamber.

In a preferred embodiment, the chamber is configured so that the cyclone interacts with the drug laden air flow so as to cause the drug laden air flow to assume a helical path as it flows from the inlet port to the outlet port.

Although it is known to provide an inhaler with a bypass air entry inlet, the sole purpose of that inlet or, more specifically, the bypass air which flows into the device through that inlet, is to reduce the overall pressure drop across the device and so make it easier for the patient to inhale. The bypass air inlets are arranged so that the bypass airflow is flowing in the same direction as the drug laden air when the two airflows meet so that there is limited interaction between the bypass air and the drug laden air.

In one embodiment, the chamber is tapered. However, the walls of the chamber may also be straight, i.e. parallel to the longitudinal axis of the chamber.

The chamber may be tapered in a direction extending from the outlet port towards the inlet port. However, they may also taper in the opposite direction.

The inhaler of the invention preferably includes a base and the inlet port is formed in said base.

A mesh can be formed in the base and the inlet port can be formed from openings in that mesh. The mesh can be formed in a separate component attached to or inserted into an aperture in the base or, it can be formed integrally in the base.

The inlet port can be coaxial with a longitudinal axis of the chamber. Alternatively, the inlet port may be offset from the longitudinal axis of the chamber.

Conveniently, the inlet port comprises at least one opening in said base.

The or each opening may extend at an angle relative to the longitudinal axis of the chamber. However, in a preferred embodiment, the longitudinal axis of each opening is parallel to, or coaxial with, the longitudinal axis of the chamber.

Preferably, the chamber comprises an end wall opposite to the base at the other end of the chamber, the outlet port being formed in said end wall.

The end wall may comprise a mesh and the outlet port can be formed from the openings in the mesh.

The mouthpiece may have a portion that extends beyond the end wall in a direction away from the inlet port. That portion may taper outwardly away from said end wall to form a diffuser.

In a preferred embodiment, the bypass air inlet is located at the base of the chamber. Conveniently, the base forms a sidewall of the bypass air inlet.

In another embodiment, the bypass air inlet is spaced from the base closer to the end wall. In one embodiment, the bypass air inlet is adjacent to the end wall and can be partially formed from the end wall.

The tangential bypass air inlet may be formed from an arcuately shaped flow path.

In other embodiments, there can be more than one tangential bypass air inlet. Preferably, there are at least two inlets on diametrically opposite sides of the chamber.

In a preferred embodiment, the chamber is formed within a mouthpiece. However, in another embodiment, the outlet port of the chamber is connected to a separate mouthpiece. If the chamber is formed within the mouthpiece, it can be a separate component within the mouthpiece. That component may be separable from the mouthpiece.

Preferably, the inhaler comprises a blister piercing element operable to puncture the lid of a blister containing a dose of medicament to enable a user to inhale said dose through said chamber.

In one embodiment, the blister piercing member comprises a piercing element upstanding from a surface and clean air inlet and drug laden air outlet flow passages extending through the blister piercing member from said surface in the vicinity of each piercing element, said piercing element being operable to puncture a clean air inlet opening and a drug laden air outlet opening in the blister such that, when a user inhales, clean air can flow through the clean air inlet flow passage in the blister piercing member and clean air inlet opening into the blister to entrain the dose contained in the blister, the drug laden air flowing out of the blister through the drug laden air outlet opening in the blister and drug laden air outlet flow passage in the blister piercing member.

Preferably, the drug laden air outflow passage is in communication with the inlet port of the chamber.

In one preferred embodiment, the clean air inlet opening comprises a plurality of peripheral clean air inlet openings that surround the drug laden air outlet opening. Advantageously, the clean air inlet openings are arranged symmetrically around the drug laden air outlet opening.

In one embodiment, the inhaler further comprises a housing configured to receive a strip having a plurality of blisters, each blister having a puncturable lid and containing a dose of medicament for inhalation by a user, means operable to drive the strip to sequentially move each blister into alignment with the blister piercing member and actuating means operable to cause the blister piercing member to pierce the lid of said aligned blister.

In another embodiment, the inhaler comprises a housing configured to receive a single blister having a puncturable lid and containing a dose of medicament for inhalation by a user and actuating means operable to cause the blister piercing member to pierce the lid of said blister received in the housing.

Embodiments of the invention will now be described, by way of example only, with reference to the accompanying drawings, in which:—

FIG. 1 is a simplified cross-sectional side view of a portion of an inhalation device according to an embodiment of the present invention;

FIG. 2 is a cross-sectional view of the device shown in FIG. 1 taken along line X-X;

FIG. 6 is a graph comparing the Fine Particle Fraction and Fine Particle Dose obtained with a device having a bypass cyclone according to the invention, and an otherwise similar device where the bypass air flows in the same direction as the drug laden air.

Figure 3:
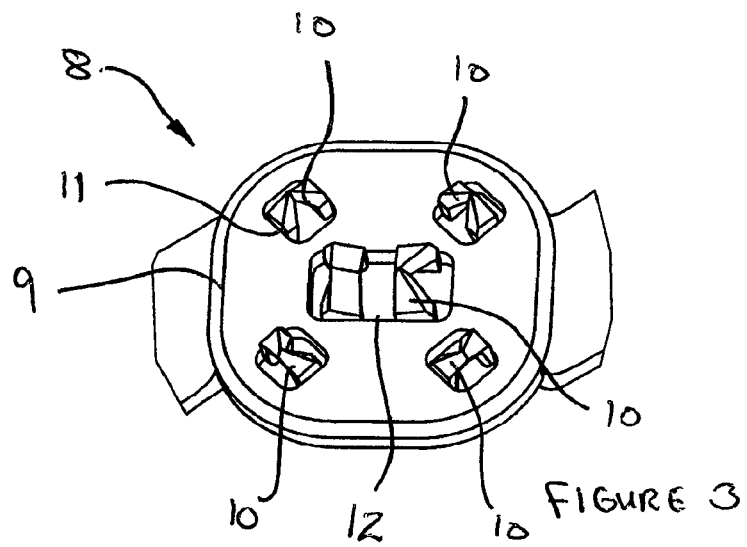
FIG. 3 is a perspective view of the blister piercing head of the inhaler shown in FIG. 1.

Referring now to the drawings, there is shown in FIG. 1 a portion 1 of an inhalation device according to an embodiment of the present invention having a mouthpiece 2 defining a chamber 3 having a chamber wall 3a, a drug laden air inlet port 4, an outlet port 5 and bypass air inlets 6. A cross-sectional view taken along the line X-X in FIG. 1 is also shown in FIG. 2.

The term "bypass" means that the air entering through these inlets 6 is clean air, i.e. air from outside the device 1 which does not have drug entrained in it.

The device includes a base 7 extending across a lower end of the mouthpiece 2 and closing the chamber 3. The drug laden air inlet port 4 is formed in, and extends through, the base 7. In the illustrated embodiment, the drug laden air inlet port 4 is coaxial with the longitudinal axis (A-A in FIG. 1) of the chamber 3, although it will be appreciated that the drug laden air inlet port 4 may be offset or otherwise spaced from the longitudinal axis. The axis of the drug laden air inlet port 4 may also be angled with respect to the longitudinal axis of the chamber 3, although in the preferred embodiment the axis of the drug laden air inlet port 4 is parallel to the longitudinal axis of the chamber 3. It is also possible that the base 7 may have multiple drug laden air inlet ports 4 positioned around the longitudinal axis of the chamber 3.

Although the base 7 could be formed integrally with the mouthpiece 2, it is preferably formed as a separate component which is attached to the mouthpiece 2 during assembly. The mouthpiece 2 and base 7 may also be separable from each other by a user to facilitate cleaning of the inside of the chamber 3.

Figure 4:
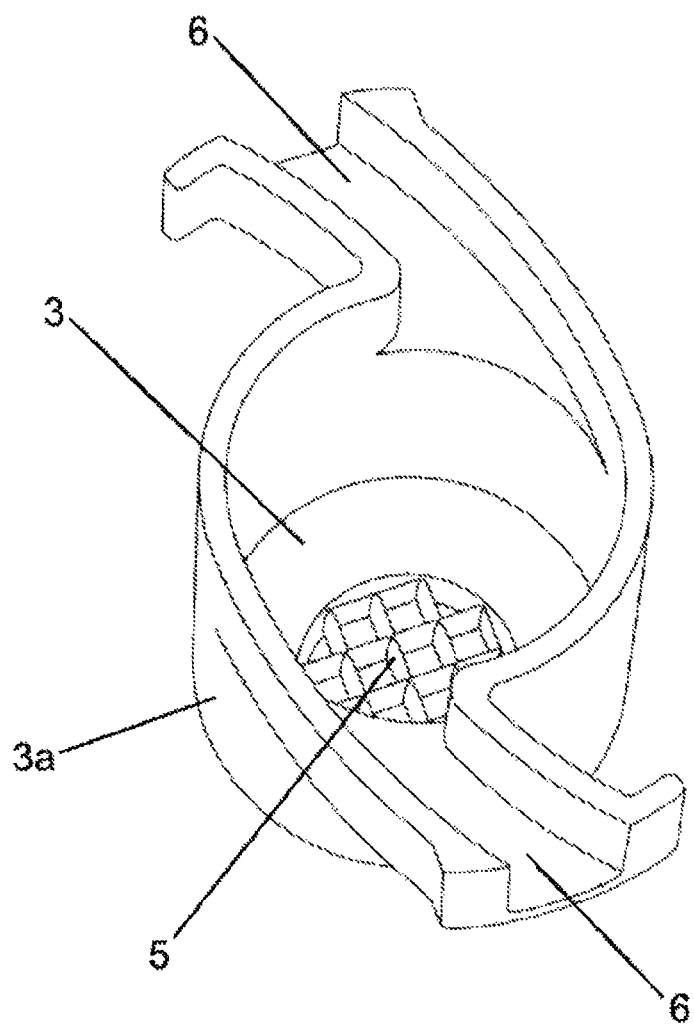
FIG. 4 is a perspective view of the cyclone chamber without the mouthpiece of the inhalation device shown in FIG. 1 or 2.

As can be seen most clearly from FIGS. 2 and 4, which shows an underside perspective view of the mouthpiece 2 without the base 7, the bypass air inlets 6 are channels formed in the sides of the mouthpiece 2 and the base 7 forms the lowermost wall and encloses the lower end of the chamber (apart from the drug laden air inlet port 4), but also forms the lower surface of the channels 6 so that the channels 6 are open only at each of their ends. In the illustrated embodiment, there are two bypass air inlets 6 so as to direct clean air into the chamber 3. However, there may only be one or several bypass air inlets 6. The bypass air inlets 6 are preferably tangential to the chamber 3, although it will be appreciated that the desired air flow can also be obtained as a result of positioning the bypass air inlets 6 so that they are not at an exact tangent to the chamber 3 but are offset from it.

In the illustrated embodiment, the bypass air inlets 6 are arcuate in shape, although they may also be straight. They may also be circular in cross-section and/or taper along their length in either direction.

The base 7 has columns 15 which slidably align the chamber 3 and the channels 6 to the base when the inhaler is assembled. In the illustrated embodiment shown in FIG. 2, the channels 6 terminate in a flange 17 such that each channel 6 and flange 17 abuts one of the columns 15.

As the bypass air inlets 6 are arranged tangentially or so as to direct the bypass air in a substantially tangential direction into the chamber 3, the clean air flowing through these inlets 6 into the chamber 3 spins around the chamber so as to form a cyclone or vortex (as indicated by arrow "B" in FIG. 1).

The outlet port 5 may be in the form of a mesh extending across the end of the chamber 3 through which the entrained drug may flow out of the chamber 3 into the patient's airway. Preferably, the mouthpiece 2 incorporates a flow diffuser 5a that extends beyond the outlet port 5 and has a cross-sectional area that gradually increases towards the top edge 2a of the mouthpiece 2. The walls 2b of the diffuser 5a in this region may be curved in shape.

The chamber 3 may be straight, i.e. the inner curved surface 3a of the chamber 3 may extend parallel to the longitudinal axis of the chamber 3. However, in other embodiments, the chamber 3 may taper in either direction. In particular, it may widen as it extends from the drug laden air inlet 4 towards the outlet port 5.

The diameter and height of the chamber 3 have been shown to influence the aerosolisation performance. Preferably the diameter of the chamber 3 is between 15 mm and 25 mm and the height is 20 mm or more. However, to be able to package a device into a convenient volume, smaller diameters and heights have also been used to get a sufficient increase in performance with less demanding therapies. In these cases diameters down to 9.5 mm and heights down to 5.5 mm have been shown to give significant improvements in aerosolisation over a device without cyclonic bypass air.

Air inlets 6 of dimensions 3.7 mm wide and 5.6 mm high have been shown to work well although, surprisingly, the aerosolisation performance is less sensitive to the cross sectional area of the air inlets 6 which may then be advantageously varied to modify the resistance of the device to suit a particular therapy/patient group with little impact on performance.

A piercing device 8 is disposed beneath the mouthpiece 2 on the opposite side of the base 7 and may extend from or be connected to the base 7. As can most clearly be seen from FIG. 3, the piercing device 8 comprises a piercing head 9 having piercing elements 10 depending therefrom. The piercing head 9 has clean air inlet flow passages 11 spaced around a central drug laden air outlet passage 12 (see FIG. 3). In one embodiment, the inhaler 1 is configured to receive a single blister 13 containing a dose of medicament which is located beneath the blister piercing elements 10. The blister piercing elements 10 are configured to puncture the lid 13a of said blister 13 so that, when a patient inhales through the mouthpiece 2, clean air enters the blister 13 through the air inlet flow passages 11 (in the direction of arrow "C" in FIG. 1) and entrains the dose contained in the blister 13. The drug laden air then flows out of the blister 13 through the central drug laden air outlet passage 12 (in the direction of arrow "D"). The drug laden air outlet passage 12 is connected to the drug laden air inlet port 4 of the chamber 3 so that it flows in an axial direction into the chamber 3 (in the direction indicated by arrow "E"). At the same time, clean bypass air enters the chamber 3 through the tangential bypass air inlets 6 and spins around the chamber 3 (in the direction of arrow "B") forming a vortex or cyclone.

It will be appreciated from FIG. 3, that the air inlet flow passages 11 and drug outlet flow passage 12 are symmetrically arranged so the emitted drug dose has no dependence on the orientation of the inhaler around the chamber axis at the time of inhalation. The blister piercing elements 10 extend over or bridge the air inlet flow passages 11 and drug outlet flow passage 12. The drug outlet flow passage 12 may be larger than the total combined area of the air inlet flow passages to increase flow area and to ensure that as much as possible of the dose is entrained in the airflow and removed from the blister 13.

Although reference is made to a unit dose device which receives only one blister 13 at a time, the invention is equally applicable to a multi-dose dry powder inhaler. For example, the device may have a housing configured to receive a strip having a plurality of blisters spaced along its length and means which are operable to drive the strip to sequentially move each blister into alignment with the blister piercing member. Such a device may also be provided with an actuator to cause the blister piercing member to pierce the lid of an aligned blister. A device of this type is known, for example, from the Applicant's own earlier application published as WO05/037353 A1.

The cyclone interacts with the drug laden air flowing in a generally axial direction between the inlet and outlet ports 4,5 so as to cause the drug laden air flow to twist or follow a helical path towards the outlet port 5. The interaction of the vortex formed from the bypass air spinning around chamber 3 on the drug laden air flowing into the chamber 3 in an axial direction has been found by the Applicant to provide a marked improvement in performance of the inhaler. Experimental results have shown that the drug laden air is accelerated as it flows through the chamber 3 and experiences increased shear forces and differential velocities which further deagglomerates the particles and improves the fine particle fraction of the emitted dose.

FIG. 6 is a graph which compares aerosolisation performance, for a typical drug and fill weight, of the cyclone bypass air invention and an otherwise similar device where the bypass airflow is flowing in the same direction as the drug laden air with limited interaction between the bypass air and the drug laden air.

This graph illustrates approximately 200% increase in fine particle fraction with the cyclone bypass device.

In the illustrated embodiment, the chamber 3 is provided within the mouthpiece 2. This has the advantage that the contact area between the device and drug dose is minimised as there is no additional airway to carry the deagglomerated drug into the mouthpiece for delivery to the user and the device is compact. However, it will be appreciated that the mouthpiece 2 could be separate to the chamber 3 in which case a further flow path extends from the outlet 5 of the chamber 3 to the inlet of the separate mouthpiece. The chamber 3 may also be a separate component that is inserted within the mouthpiece 2 and could be detachable therefrom. A separate chamber unit is shown in FIG. 4, which locates within the mouthpiece 2, as shown in FIGS. 1 and 2.

Figure 5:
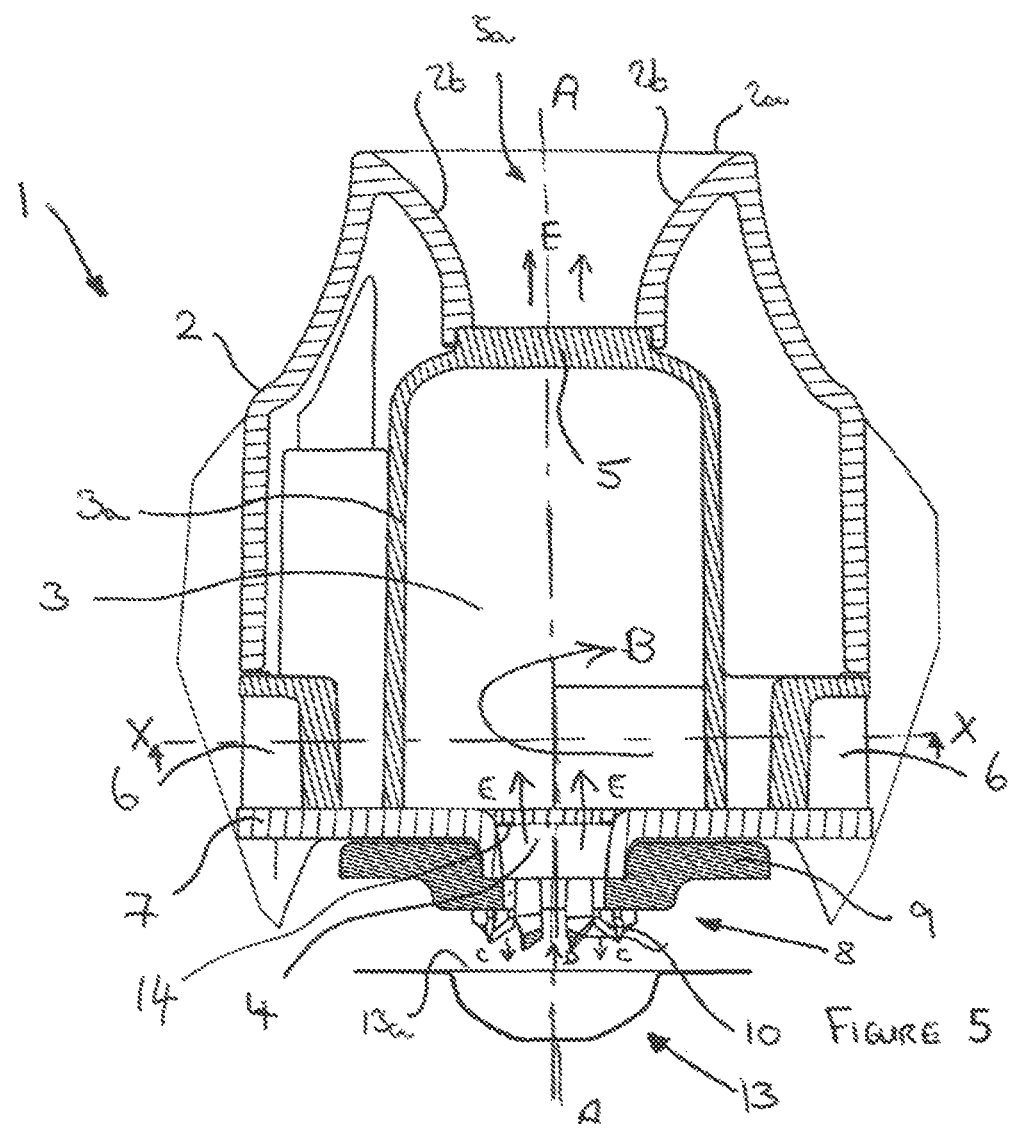
FIG. 5 is a simplified cross-sectional side view of a portion of an inhalation device according to an embodiment of the present invention, showing a mesh, the inlet port being formed by the openings in the mesh.

In the illustrated embodiment of FIG. 5, the base 7 includes a mesh portion 14, with the inlet port being formed by the openings in said mesh.

Many modifications and variations of the invention falling within the terms of the following claims will be apparent to those skilled in the art and the foregoing description should be regarded as a description of the preferred embodiments of the invention only.

The invention claimed is:

1. An inhaler for producing an inhalable aerosol of powdered medicament including an aerosolising device comprising:
    a chamber of substantially circular cross-section defined by an inner curved surface and having a longitudinal axis located in the center of the chamber;
    an inlet port for the flow of drug laden air into the chamber which is coaxial with said longitudinal axis of the chamber;
    an outlet port at the opposite end of the chamber such that drug laden air flows through the chamber between said ports and out of the chamber through the outlet port;
    two bypass air inlets for the flow of clean air into the chamber in a tangential direction, wherein said bypass air inlets are configured so that air entering the chamber through said bypass air inlets forms a cyclone in the chamber that interacts with the drug laden air as the drug laden air flows between the inlet and outlet ports, wherein the bypass air inlets include elongated channels which are arcuate in shape, with said elongated channels having sides and a roof, with each channel extending horizontally from a first aperture open to an exterior of the inhaler to a second aperture formed in a curved inner surface of and leading into the chamber such that clean air enters the chamber in a tangential direction to said curved inner surface and forms said cyclone about the longitudinal axis of the chamber along which the drug laden air is flowing between the inlet and outlet ports;
    a base which forms a bottom surface of the chamber and of the two elongated channels, said base having an opening to form the inlet port for the flow of drug laden air into the chamber and having columns which slidably align the chamber and the elongated channels to the base when the inhaler is assembled;
    wherein the inhaler is a dry powder inhaler.

2. An inhaler according to claim 1, wherein the chamber is configured so that the cyclone interacts with the drug laden air flow so as to cause the drug laden air flow to assume a helical path as it flows from the inlet port to the outlet port.

3. An inhaler according to claim 1, wherein the chamber is tapered.

4. An inhaler according to claim 3, wherein the chamber tapers in a direction extending from the outlet port towards the inlet port.

5. An inhaler according to claim 3, wherein the chamber tapers in a direction extending from the inlet port towards the outlet port.

6. An inhaler according to claim 1, wherein the base includes a mesh portion, the inlet port being formed by the openings in said mesh.

7. An inhaler according to claim 1, wherein the inlet port comprises at least one opening in the base.

8. An inhaler according to claim 7, wherein each opening extends through the base at an angle relative to the longitudinal axis of the chamber.

9. An inhaler according to claim 1, wherein the chamber comprises an end wall at the other end of the chamber opposite the base, the outlet port being formed in said end wall.

10. An inhaler according to claim 9, wherein the end wall comprises a mesh, the outlet port being formed from openings in the mesh.

11. An inhaler according to claim 9, wherein the chamber has a portion that extends beyond the end wall in a direction away from the inlet port.

12. An inhaler according to claim 11, wherein said portion tapers outwardly away from said end wall to form a diffuser.

13. An inhaler according to claim 1, wherein the chamber is formed within a mouthpiece.

14. An inhaler according to claim 13, wherein the chamber is a separate component received within the mouthpiece.

15. An inhaler according to claim 14, wherein said separate component is separable from the mouthpiece.

16. An inhaler according to claim 1, wherein the outlet port of the chamber is connected to a separate mouthpiece.

17. An inhaler according to claim 1, comprising a blister piercing element operable to puncture a lid of a blister containing a dose of medicament to enable a user to inhale said dose through said chamber.

18. An inhaler according to claim 17, wherein the blister piercing element comprises a piercing element upstanding from a surface and clean air inlet and drug laden air outlet flow passages extending through the blister piercing member from said surface in the vicinity of each piercing element, said piercing element being operable to puncture a clean air inlet opening and a drug laden air outlet opening in the blister such that, when a user inhales, clean air can flow through the clean air inlet flow passage(s) in the blister piercing member and clean air inlet opening(s) into the blister to entrain the dose contained in the blister, the drug laden air flowing out of the blister through the drug laden air outlet opening in the blister and drug laden air outlet flow passage in the blister piercing member.

19. An inhaler according to claim 18, wherein the drug laden air outflow passage is in communication with the inlet port of the chamber.

20. An inhaler according to claim 18, wherein the clean air inlet opening comprises a plurality of clean air inlet openings that surround the drug laden air outlet opening.

21. An inhaler according to claim 20, wherein the clean air inlet openings are arranged symmetrically around the drug laden air outlet opening.

22. An inhaler according to claim 17, comprising a housing configured to receive a strip having a plurality of blisters, each blister having a puncturable lid and containing a dose of medicament for inhalation by a user, means operable to drive the strip to sequentially move each blister into alignment with the blister piercing member and actuating means operable to cause the blister piercing member to pierce the lid of said aligned blister.

23. An inhaler according to claim 17, comprising a housing configured to receive a single blister having a puncturable lid and containing a dose of medicament for inhalation by a user and actuating means operable to cause the blister piercing member to pierce the lid of said blister received in the housing.

24. The inhaler of claim 1, having a mouthpiece which has columns which fit together in a mating connection with the columns of the base when the inhaler is assembled.

25. The inhaler of claim 1, wherein the base is detachable from the chamber and the elongated channels.

26. The inhaler of claim 1, wherein the elongated channels terminate in a flange at the first aperture such that each channel and flange abuts one of the columns.

27. The inhaler of claim 1, having a mouthpiece which has apertures positioned to allow air to enter the bypass inlets.

* * * * *